United States Patent
Herfert et al.

(10) Patent No.: US 9,422,221 B2
(45) Date of Patent: Aug. 23, 2016

(54) METHOD FOR THE RESTABILIZATION OF (METH)ACRYLIC MONOMERS

(75) Inventors: Norbert Herfert, Altenstadt (DE); Ulrich Hammon, Mannheim (DE); Renate Wuestefeld, Speyer (DE)

(73) Assignee: BASF SE, Ludwigshafen (DE)

( * ) Notice: Subject to any disclaimer, the term of this patent is extended or adjusted under 35 U.S.C. 154(b) by 1128 days.

(21) Appl. No.: 13/375,109

(22) PCT Filed: May 31, 2010

(86) PCT No.: PCT/EP2010/057519
§ 371 (c)(1),
(2), (4) Date: Nov. 29, 2011

(87) PCT Pub. No.: WO2010/142546
PCT Pub. Date: Dec. 16, 2010

(65) Prior Publication Data
US 2012/0074354 A1    Mar. 29, 2012

Related U.S. Application Data

(60) Provisional application No. 61/184,865, filed on Jun. 8, 2009.

(30) Foreign Application Priority Data

Jun. 8, 2009  (DE) .................. 10 2009 026 822

(51) Int. Cl.
| | | |
|---|---|---|
| C07C 51/47 | (2006.01) | |
| C09K 15/08 | (2006.01) | |
| C08K 3/04 | (2006.01) | |
| C07C 51/50 | (2006.01) | |
| C08K 5/13 | (2006.01) | |

(52) U.S. Cl.
CPC ............. *C07C 51/47* (2013.01); *C07C 51/50* (2013.01); *C08K 5/13* (2013.01)

(58) Field of Classification Search
None
See application file for complete search history.

(56) References Cited

U.S. PATENT DOCUMENTS

| | | |
|---|---|---|
| 4,590,301 A | 5/1986 | Lim et al. |
| 5,763,658 A | 6/1998 | Beihoffer et al. |
| 2006/0089512 A1 | 4/2006 | Bennett et al. |

FOREIGN PATENT DOCUMENTS

| | | | |
|---|---|---|---|
| EP | 0 179 476 | | 4/1986 |
| EP | 0 775 686 | | 5/1997 |
| JP | 50061391 | * | 5/1975 |
| JP | 08310979 | * | 11/1996 |
| WO | 2004 052819 | | 6/2004 |

OTHER PUBLICATIONS

Norit Activated Carbon Datasheet. May 2009.*
International Search Report Issued Jan. 26, 2011 in PCT/EP10/057519 Filed May 31, 2010.

* cited by examiner

*Primary Examiner* — Tanisha Diggs
(74) *Attorney, Agent, or Firm* — Oblon, McClelland, Maier & Neustadt, L.L.P

(57) ABSTRACT

A process for replacing the stabilization of (meth)acrylic monomers, wherein phenothiazine is removed from phenothiazine-containing (meth)acrylic monomers by adsorption on activated carbon, and then a moderately active polymerization inhibitor is optionally added.

18 Claims, No Drawings

METHOD FOR THE RESTABILIZATION OF (METH)ACRYLIC MONOMERS

The present invention relates to a process for replacing the stabilization of (meth)acrylic monomers.

In the context of the present invention, the term "(meth) acrylic monomers" is understood to mean substances which consist of acrolein, methacrolein, acrylic acid, methacrylic acid and/or of esters of the two aforementioned acids. "(Meth)acrylic" is used in this document generally as an abbreviated notation for acrylic and/or methacrylic.

(Meth)acrylic monomers are ethylenically unsaturated compounds which can polymerize by a free-radical mechanism. Once triggered, the free-radical polymerizations normally proceed in a markedly exothermic manner, i.e. with significant evolution of heat, and the heat of polymerization released, if it is not removed, additionally accelerates the free-radical polymerization.

When the aforementioned heat removal is inadequate in the case of intentional free-radical polymerizations, there is the risk that the polymerization will proceed so violently that the vessel containing the polymerization mixture explodes unless the polymerization, having got out of control, is counteracted.

Such an effective counteraction is required especially in the case of inadvertently triggered free-radical polymerizations. Inadvertently triggered free-radical polymerizations can occur, for example, in the course of storage and/or in the course of transport of substances comprising monomers, since both heat and light or undesired free radicals can trigger a free-radical polymerization of monomers. Attempts are made to preventively counteract such inadvertent free-radical polymerizations typically by adding a small amount (generally up to 1000 ppm) of polymerization inhibitors to the monomers. However, the inhibiting action must not be too marked, since the monomers have to be subjected to an intended free-radical polymerization for the later use thereof. A moderately inhibiting action, as possessed, for example, by hydroquinone monomethyl ether (MEHQ), can, however, normally be dominated by free-radical polymerization initiators, which is why MEHQ is a particularly common storage and/or transport stabilizer for monomers. However, experience has shown that, even in the case of monomers stabilized with storage and/or transport stabilizers, inadvertent free-radical polymerization thereof cannot be completely ruled out. This is especially true of the particularly readily polymerizable (meth)acrylic monomers, especially of (meth)acrylic acid.

(Meth)acrylic monomers tend to polymerize particularly when such substances are exposed to extreme external conditions in the course of transport and/or in the course of storage (for example extremely high temperatures in the course of transport by ship through different climate zones, as is the case, for example, in the case of transport from Europe to South-East Asia or South America.

For safe transport of (meth)acrylic monomers, they are typically stablized with phenothiazine (PTZ) or mixtures of PTZ with other polymerization inhibitors. PTZ is an exceptionally active stabilizer for (meth)acrylic monomers. However, further processing of the PTZ-containing (meth)acrylic monomers is virtually impossible, since polymerization is prevented in the presence of PTZ. PTZ-containing (meth)acrylic monomers therefore have to be purified before further processing, by completely removing PTZ. This removal is effected typically by distillation or crystallization, as described, for example, in WO 05/007610 A1 and in WO 02/090299 A2.

A disadvantage of this is that the removal of the PTZ from the (meth)acrylic monomers by distillation and crystallization is very complex, especially because the (meth)acrylic monomers first have to be converted to the gaseous or solid state in order to be able to completely remove the PTZ. Secondly, another, moderately inhibiting stabilizer, for example MEHQ, has to be added, in order that an inadvertent free-radical polymerization before the planned further processing is still prevented.

EP 0 775 686 A1 discloses a process for adsorptive separation of PTZ from acrylic acid. Accordingly, a PTZ-containing acrylic acid solution is contacted with a bentonite in order to reduce the PTZ content to less than 100 ppm. A disadvantage of this process is that the PTZ content after adsorption is still too high to send the acrylic acid to further processing.

It was therefore an object of the present invention to provide a process for replacing the stabilization of (meth)acrylic monomers, in which phenothiazine is removed effectively and simply from phenothiazine-containing (meth) acrylic monomers and, if necessary, a moderately active polymerization inhibitor which does not significantly hinder further processing is then added.

This object is achieved by a process for replacing the stabilization of (meth)acrylic monomers, wherein phenothiazine is removed from phenothiazine-containing (meth) acrylic monomers by adsorption on activated carbon, and then a moderately active polymerization inhibitor is optionally added.

What is advantageous about the process according to the invention is that the adsorptive removal of the PTZ is simple and virtually complete. It is particularly advantageous that the (meth)acrylic monomers in the liquid state, as present, for example, in the course of transport, can be supplied directly to the adsorption. Typically, (meth)acrylic monomers comprise up to 1000 ppm, preferably up to 500 ppm and especially around 200 ppm of phenothiazine as a polymerization inhibitor. (Meth)acrylic monomers stabilized in this way can be transported without risk even over long distances.

For the inventive purification of (meth)acrylic monomers by adsorption on activated carbon, it is possible to use adsorption processes as described, for example, in Ullmann's Enzyklopädie der Technischen Chemie, 4th edition, vol. 2, p. 600-619 and in the literature cited there, and as known to those skilled in the art. These are, for example, fixed bed processes in which the activated carbon is arranged in a fixed bed and the (meth)acrylic monomer to be purified flows through in the flooded state, i.e. downward in the pebble phase, or else from the bottom upward.

In terms of the design of the fixed bed adsorber, a distinction is drawn, for example, between horizontal or vertical adsorbers and simple adsorption tanks. Other adsorption processes work instead with moving adsorbents, for example in a moving bed or in a fluidized bed. In the case of use of pulverulent activated carbons, an additional distinction is drawn between stir-in processes, in which the adsorbent is stirred with the (meth)acrylic monomer to be purified in a stirred vessel and then filtered off in a filter press, and the process of layer filtration, in which flotation on the filter first produces an adsorbent layer, through which the (meth)acrylic monomer to be purified is forced.

For the inventive purification of (meth)acrylic monomers by adsorption on activated carbon, preference is given to employing fixed bed processes. Advantageously, two adsorption beds are provided, in order to be able to switch to the other in the event of exhaustion of one adsorption bed, and to regenerate or replace the spent activated carbon. Conceivable options are therefore either a parallel connection of two adsorption beds or, preferably, a series arrangement of two adsorption beds. Particular preference is given to the use of four adsorption beds in the form of a parallel arrangement of two adsorption beds each in series. This particularly preferred embodiment can ensure that, on exhaustion of the first adsorption beds, the second adsorption beds connected in series in each case sufficiently remove residual PTZ from the (meth)acrylic monomers. According to the process selected, a filtration step must be connected downstream of the inventive purification of the (meth)acrylic monomer by adsorption.

The parameters to be established in the inventive purification of the (meth)acrylic monomer by adsorption, such as temperature, pressure, residence time, depend on the selection of the adsorption process and influence the result of the purification in a manner known to the person skilled in the art. For example, for the purification of the (meth)acrylic monomer, a temperature above the melting point of the particular (meth)acrylic monomer has to be maintained. The maximum possible is the boiling temperature of the particular (meth)acrylic monomer. In the case of acrylic acid, the melting point under standard conditions is 14° C., the boiling temperature 141° C. The melting and boiling points of the particular (meth)acrylic monomers to be purified vary, of course, with the degree of purity thereof.

In principle, the adsorption temperature to be established is thus 15 to 140° C., preferably 20 to 100° C. and more preferably 20 to 80° C. Particular preference is given to performing the adsorption at ambient temperature. The pressure should be in the range from 1 to 100 bar, preferably 1 to 10 bar, more preferably 1 to 5 bar.

In the context of the present invention, activated carbon is understood to mean activated carbon which can be produced from different carbon-supplying precursors. The processes for conversion to the active form may likewise be very different. Such production processes afford activated carbons which have BET surface areas of 200 to 3000 $m^2/g$, preferably 300 to 2000 $m^2/g$, more preferably 500 to 1800 $m^2/g$ and bulk densities between 250 and 550 g/l.

Examples of starting materials for producing activated carbons include: sawdust and other wood wastes, straw, various coal types, such as bituminous or brown coal, nutshells, for example coconut, mineral oil tars, lignin, polysaccharides, polyacrylonitrile, bones or peat. In addition, it is also possible to use coking products from brown and hard coals. Preferred examples include: wood, cellulose, lignin, bituminous or brown coal, nutshells, peat or coke from hard coal.

The carbon-supplying precursors mentioned can be activated by various methods, for example by chemical activation with phosphoric acid or zinc chloride, by gas activation with steam, oxygen or gases comprising nitrous. Such preactivated precursors are then converted thermally, i.e. by coking, to activated carbons for the process according to the invention. These preparation methods are known to those skilled in the art and are described in detail in the literature, as is a more detailed description of the different types of activated carbon (see Ullmann's Encyclopedia of Industrial Chemistry, 5th ed., vol. A5 (1986), p. 124-140 and literature cited there).

With regard to the use form, it is possible to use molded carbons, granular carbons and pulverulent carbons in the process according to the invention. In the case of molded carbons, which are usually produced by extrusion from powders and then have a cylindrical shape or more rarely are present in the form of pellets, usual diameters are in the range from one to a few mm. In the case of pulverulent carbons, particular attention has to be paid to sufficient filterability.

The person skilled in the art is aware of the optimal application form of the activated carbon, which depends on the selection of the adsorption process.

Regeneration of the activated carbon is possible in principle and can also be performed depending on economic viability. The adsorbed salts and coloring compounds can optionally be washed off the activated carbon with water, with methanol, methanol/water, with glycol or with glycol-water mixtures, and regeneration can be achieved in this way. In a continuous mode of operation, the activated carbon used can remain in the adsorber over a long period. Insoluble organic deposits can be removed by passing over superheated steam, optionally with addition of minor amounts of air (about 0.1 to 20% by weight, based on the amount of steam used) at 150 to 800° C., or by passing over dilution gases, such as nitrogen, carbon monoxide or carbon dioxide, comprising 0.01 to 5% by weight of oxygen, or by means of carbon dioxide alone, at 200 to 800° C. The preferred regeneration temperature is 250 to 700° C., more preferably 250 to 600° C.

For the process according to the invention, suitable activated carbons are especially commercially available activated carbons, for example CPG® LF from Chemviron Carbon (BET 950-1050 $m^2/g$), CAL® from Chemviron Carbon (BET 1050 $m^2/g$), Epibon® Y 12×40 from Donau Carbon (BET 1000 $m^2/g$), Norit® GAC 1240 N from Norit (BET 1125 $m^2/g$), Norit® ROX 0,8 Supra from Norit (BET 1225 $m^2/g$), Acticarbone® BGX from Ceca Chemicals (BET surface area not stated), pulverulent activated carbon from Carl Roth (BET surface area not stated), Norit® CAP Super from Norit (BET 1800 $m^2/g$) and Norit® CA1 from Norit (BET 1400 $m^2/g$).

(Meth)acrylic monomers purified by adsorption are virtually free of PTZ, i.e. the PTZ content after adsorption is generally less than 10 ppm, based on the (meth)acrylic monomers, preferably less than 5 ppm, more preferably less than 3 ppm, based in each case on the (meth)acrylic monomers.

If required, it is subsequently possible to add another, moderately active polymerization inhibitor, in order that the (meth)acrylic monomers are not exposed to an inadvertent free-radical polymerization before further processing. The moderately active polymerization inhibitor can be added either before the adsorbing treatment or during the adsorbing treatment when the moderately active polymerization inhibitor is not adsorbed or is adsorbed only to a minor degree during the adsorptive treatment. When the moderately active polymerization inhibitor is adsorbed to a considerable degree, it is favorably added directly after the treatment. For example, this moderately active polymerization inhibitor can be added in the customary amounts, such that the inhibitor content is up to 1000 ppm, preferably up to 500 ppm, more preferably up to 200 ppm, most preferably up to 100 ppm and especially around 50 ppm, based in each case on the (meth)acrylic monomers.

It is likewise possible that an addition of a moderately active polymerization inhibitor is not required, especially when the (meth)acrylic monomers are already stabilized sufficiently with such an inhibitor in order to prevent an inadvertent free-radical polymerization before further processing. Such a sufficient stabilization is present when the inhibitor content is already up to 250 ppm, preferably at most 130 ppm, more preferably at most 70 ppm, preferably at least 10 ppm, more preferably at least 30 ppm, especially around 50 ppm, of moderately active polymerization inhibitor, based in each case on the (meth)acrylic monomer.

A moderately active polymerization inhibitor in the context of the present invention is selected from the group of the phenolic compounds and quinones.

Phenolic compounds which optionally have one or more alkyl groups, for example alkylphenols, are understood to mean, for example, o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol.

Quinones are likewise suitable as moderately active polymerization inhibitors and are, for example, hydroquinone, hydroquinone monomethyl ether, 2-methylhydroquinone, 2,5-di-tert-butylhydroquinone or benzoquinone.

Among the aforementioned moderately active polymerization inhibitors, quinones are preferred, particular preference being given to hydroquinone and hydroquinone monomethyl ether (MEHQ), and MEHQ being especially preferred.

It has been found that, surprisingly, the process according to the invention particularly effectively and selectively removes PTZ, but any moderately active polymerization inhibitor likewise present, such as MEHQ, remains in the (meth)acrylic monomer in relatively large amounts. This is surprising especially with regard to WO 03/051940 A1, WO 2004/052819 A2 and JP 48-43331. According to the teaching of WO 03/051940A1, MEHQ in unneutralized acrylic acid is reduced by the adsorptive separation on activated carbon to a content of 10 to 160 ppm. WO 04/0552819 A2 and JP 48-43331 disclose the adsorptive removal of MEHQ on activated carbon in partly to fully neutralized acrylic acid. The present invention shows, however, that PTZ is removed significantly more effectively than, for example, EHQ.

The process according to the invention is suitable especially for (meth)acrylic acid and more preferably for acrylic acid. Acrylic acid is stored and transported globally in large amounts, for example in order to prepare superabsorbent polymers therefrom in other countries. The preparation of acrylic acid is known per se and is described, for example, in WO 02/090299 A2, WO 05/007610 A1 and WO 06/092410 A1.

For the preparation of superabsorbent polymers, for example, an acrylic acid with the following specification is used: 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

For the preparation of superabsorbent polymers, in addition to the acrylic acid mentioned, suitable crosslinkers, initiators and optionally copolymerizable ethylenically unsaturated monomers are also added. Such compounds and the preparation of superabsorbent polymers are known to the person skilled in the art, for example, from Ullmanns's Encyclopedia of Industrial Chemistry. 6th Ed., Viley VCH, 2003 Vol. 35, "Superabsorbents", p. 73-93.

Typically, an aqueous acrylic acid solution is used for the preparation of the superabsorbent polymers. The water content of the acrylic acid solution is preferably from 40 to 75% by weight, more preferably from 45 to 70% by weight, most preferably from 50 to 65% by weight. The process according to the invention is therefore also suitable for acrylic acid solutions with a corresponding water content of 40 to 75% by weight.

The process according to the invention, however, is preferably performed on acrylic acid solutions to which no water has yet been added and which are thus anhydrous. "Anhydrous" means that the water content is within the range of the customary specification of acrylic acid described above, i.e. the water content is less than 1% by weight, preferably less than 0.5% by weight and more preferably less than 0.05% by weight.

Furthermore, it is customary that the acid groups of the superabsorbent polymers obtained are partly neutralized. The neutralization is preferably performed at the acrylic acid monomer stage. This is typically done by mixing in the neutralizing agent as an aqueous solution or preferably also as a solid. The degree of neutralization is preferably from 25 to 95 mol %, more preferably from 30 to 80 mol %, most preferably from 40 to 75 mol %, for which the customary neutralizing agents can be used, preferably alkali metal hydroxides, alkali metal oxides, alkali metal carbonates or alkali metal hydrogencarbonates, and mixtures thereof. Instead of alkali metal salts, it is also possible to use ammonium salts. Sodium and potassium are particularly preferred as alkali metals, but very particular preference is given to sodium hydroxide, sodium carbonate or sodium hydrogencarbonate, and mixtures thereof.

In one embodiment of the process according to the invention, it is therefore also suitable for acrylic acid monomer solutions whose acid groups have been neutralized partly with the aforementioned neutralizing agents, for example in the range from 25 to 95 mol %, preferably from 30 to 80 mol %, most preferably from 40 to 75 mol %.

In another embodiment, it is of course also possible to purify unneutralized acrylic acid monomer solutions to remove PTZ by adsorptive separation on activated carbon.

EXAMPLES

The examples which follow are intended to illustrate the properties of the invention, but without restricting it.

Unless specified otherwise, percent always means percent by weight, and parts always means parts by weight.

Monomer solution 1: Preparation of an acrylic acid-containing solution with a degree of neutralization of 72 mol % and a solids content of 41% by weight A stainless steel beaker was initially charged with 80 parts by weight of 50% by weight sodium hydroxide solution and 117.6 parts by weight of frozen deionized water. While stirring, 100 parts by weight of acrylic acid which comprised 317 ppm of phenothiazine (PTZ) and 100 ppm of hydroquinone monomethyl ether (MEHQ) were added. In the course of this, the rate of addition was adjusted such that the temperature in the mixture did not exceed 35° C. During the neutralization reaction, a precipitate formed, which was filtered off by means of a fluted filter paper. The filtered monomer solution was analyzed by means of HPLC; it comprised 27 ppm of PTZ and 29 ppm of MEHQ.

Monomer solution 2: Preparation of an acrylic acid-containing solution with a degree of neutralization of 50 mol % and a solids content of 47% by weight.

A stainless steel beaker was initially charged with 55.56 parts by weight of 50% by weight sodium hydroxide solution and 89.72 parts by weight of frozen deionized water. While stirring, 100 parts by weight of acrylic acid which comprised 317 ppm of phenothiazine (PTZ) and 100 ppm of hydroquinone monomethyl ether (MEHQ) were added. In the course of this, the rate of addition was adjusted such that the temperature in the mixture did not exceed 35° C. During the neutralization reaction, a precipitate formed, which was filtered off by means of a fluted filter paper. The filtered monomer solution was analyzed by means of HPLC; it comprised 70 ppm of PTZ and 38 ppm of MEHQ.

Example 1

Adsorption of the PTZ-Containing Monomer Solutions 1 and 2 with Activated Carbon For example 1, six different commercially available activated carbons were used. These are specifically:

Activated carbon 1: CPG® LF from Chemviron Carbon (BET 950-1050 $m^2/g$)

Activated carbon 2: CAL® from Chemviron Carbon (BET 1050 $m^2/g$)

Activated carbon 3: Epibon® Y 12×40 from Donau Carbon (BET 1000 $m^2/g$)

Activated carbon 4: Norit® GAC 1240 N from Norit (BET 1125 $m^2/g$)

Activated carbon 5: Norit® ROX 0,8 Supra from Norit (BET 1225 $m^2/g$)

Activated carbon 6: Acticarbone® BGX from Ceca Chemicals (BET surface area not stated)

The particular activated carbons used were dried at 120° C. overnight in a drying cabinet. Approx. 0.15 g, 0.75 g and 1.5 g of activated carbon were added to 150 g of each monomer solution, and the mixtures were shaken in a temperature-controllable shaking cabinet at 20° C. for approx. 18 h. The activated carbon was subsequently removed with the aid of filtration by means of a blue-band filter. The filtered solutions were analyzed for their PTZ and MEHQ contents by means of HPLC; the results are compiled in tables 1 (monomer solution 1) and 2 (monomer solution 2).

TABLE 1

Results for the PTZ-containing monomer solution 1 after adsorption with activated carbon

| Starting weight [g] of monomer solution 1 | Activated carbon | Starting weight [g] of activated carbon | Color after filtration | MEHQ [ppm] | PTZ [ppm] |
|---|---|---|---|---|---|
| 150.260 | 1 | 0.1571 | pink | 35 | 2 |
| 150.428 | 1 | 0.7613 | pale pink | 24 | <1 |
| 150.308 | 1 | 1.5204 | colorless | 16 | <1 |
| 151.228 | 2 | 0.1578 | pink | 36 | 2 |
| 153.223 | 2 | 0.7598 | almost colorless | 30 | <1 |
| 151.111 | 2 | 1.5221 | colorless | 25 | <1 |
| 150.579 | 3 | 0.1522 | pink | 36 | 3 |
| 150.119 | 3 | 0.7563 | pale pink | 26 | <1 |
| 150.556 | 3 | 1.5108 | colorless | 18 | <1 |
| 151.035 | 4 | 0.1520 | pink | 37 | 3 |
| 150.589 | 4 | 0.7558 | pale pink | 31 | <1 |
| 151.451 | 4 | 1.5061 | pale pink | 27 | <1 |
| 150.937 | 5 | 0.1507 | pink | 34 | 2 |
| 150.554 | 5 | 0.7519 | pale pink | 17 | <1 |
| 150.313 | 5 | 1.5089 | colorless | 8 | <1 |
| 150.615 | 6 | 0.1520 | pink | 37 | 2 |
| 151.968 | 6 | 0.7554 | pale pink | 32 | <1 |
| 150.671 | 6 | 1.5008 | colorless | 29 | <1 |

TABLE 2

Results for the PTZ-containing monomer solution 2 after adsorption with activated carbon

| Starting weight [g] of monomer solution 1 | Activated carbon | Starting weight [g] of activated carbon | Color after filtration | MEHQ [ppm] | PTZ [ppm] |
|---|---|---|---|---|---|
| 152.796 | 1 | 0.1505 | pink | 26 | <1 |
| 150.456 | 1 | 0.7529 | pale pink | 17 | <1 |
| 150.878 | 1 | 1.5161 | colorless | 11 | <1 |
| 154.246 | 2 | 0.1562 | pale pink | 26 | <1 |
| 151.007 | 2 | 0.7588 | almost colorless | 18 | <1 |
| 150.829 | 2 | 1.5089 | colorless | 11 | <1 |
| 150.928 | 3 | 0.1570 | pink | 25 | <1 |
| 153.776 | 3 | 0.7564 | pale pink | 16 | <1 |
| 150.606 | 3 | 1.5041 | colorless | 11 | <1 |
| 151.201 | 4 | 0.1524 | pink | 27 | <1 |
| 150.318 | 4 | 0.7589 | pale pink | 22 | <1 |
| 150.415 | 4 | 1.5137 | pale pink | 17 | <1 |
| 150.832 | 5 | 0.1559 | pink | 23 | <1 |
| 150.074 | 5 | 0.7520 | pale pink | 11 | <1 |
| 151.192 | 5 | 1.5047 | colorless | 5 | <1 |
| 150.450 | 6 | 0.1611 | pale pink | 26 | <1 |
| 150.789 | 6 | 0.7604 | pale pink | 21 | <1 |
| 151.723 | 6 | 1.5212 | colorless | 16 | <1 |

Example 2

Adsorption of PTZ-Containing Unneutralized Acrylic Acid Solutions (Water Content 0% by Weight or 20% by Weight)

For example 2, two different commercially available activated carbons were used. These are specifically:

Activated carbon 7: Pulverulent activated carbon from Carl Roth (BET surface area not stated)

Activated carbon 8: Norit® CAP Super from Norit (BET 1800 $m^2/g$)

20.0 g of acrylic acid each time were weighed into a 50 mL penicillin bottle. The acrylic acid solutions with water content 0% by weight comprised 239 ppm of PTZ for stabilization, and those with water content 20% by weight comprised 196 ppm of PTZ. The solutions were stirred at 400 rpm on a magnetic stirrer. Subsequently, 5% by weight of an activated carbon, based on the acrylic acid content, were added. The mixtures were stirred at room temperature for 3 h. Subsequently, samples were taken in each case, and were first filtered through a syringe filter and then analyzed for their PTZ content by means of HPLC. The results are summarized in table 3.

Comparative Example 1

Example 2 was repeated, except that the acrylic acid solutions were stabilized with 177 ppm (water content 0% by weight) or 140 ppm (water content 20% by weight) of MEHQ The results are compiled in table 3.

TABLE 3

Results for the PTZ- or MEHQ-containing acrylic acid solutions after adsorption with activated carbon

| | Water content [% by wt.] | Activated carbon | PTZ or MEHQ [ppm] | % PTZ or MEHQ removed |
|---|---|---|---|---|
| Example 2 (PTZ-containing) | 0 | 7 | 4 | 98.3 |
| | 20 | 7 | 2 | 99.0 |
| | 0 | 8 | 0 | 100.0 |

TABLE 3-continued

Results for the PTZ- or MEHQ-containing acrylic acid
solutions after adsorption with activated carbon

| | Water content [% by wt.] | Activated carbon | PTZ or MEHQ [ppm] | % PTZ or MEHQ removed |
|---|---|---|---|---|
| Comparative example 1 (MEHQ-containing) | 0 | 7 | 146 | 17.5 |
| | 20 | 7 | 124 | 11.4 |
| | 0 | 8 | 130 | 26.6 |

Example 3

Adsorption of PTZ-Containing Partly Neutralized Acrylic Acid Solutions (Water Content 60% by Weight)

For example 3, three different commercially available activated carbons were used. These are specifically:
Activated carbon 7: Pulverulent activated carbon from Carl Roth (BET surface area not stated)
Activated carbon 8: Norit® CAP Super from Norit (BET 1800 m²/g)
Activated carbon 9: Norit® CA1 from Norit (BET 1400 m²/g)

79.61 g of a 50% by weight sodium hydroxide solution were added to 100.0 g each time of a 99.6% by weight acrylic acid solution which was stabilized with 185 ppm of PTZ (degree of neutralization 72 mol %). Subsequently, 169.90 g of water were added, such that the water content of the resulting solution was 60% by weight. A fine precipitate formed, which was filtered off. 0.5% by weight of an activated carbon was added to each of the filtered solutions, based on the acrylic acid content. The mixtures were stirred at room temperature for 3 h. Subsequently, samples were taken, which were first filtered through a syringe filter and then analyzed for their PTZ content by means of HPLC.
PTZ content before neutralization: 185 ppm
PTZ content after filtration, before addition of the activated carbons: 21 ppm
PTZ content (activated carbon 7): <<1 ppm
PTZ content (activated carbon 8): <<1 ppm
PTZ content (activated carbon 9): <<1 ppm

The invention claimed is:

1. A process for removing phenothiazine from a (meth)acrylic monomer, comprising:
removing phenothiazine from a phenothiazine-containing (meth)acrylic monomer by adsorption on activated carbon, and adding a moderately active polymerization inhibitor to the (meth)acrylic monomer after adsorption, wherein the moderately active polymerization inhibitor is a phenolic compound or a quinone,
wherein a content of the phenothiazine in the (meth)acrylic monomer after adsorption is less than 10 ppm.

2. The process of claim 1, wherein a BET surface area of the activated carbon is from 200 to 3000 m²/g.

3. The process of claim 2, wherein the BET surface area of the activated carbon is from 300 to 2000 m²/g.

4. The process of claim 1, wherein the activated carbon is molded carbon, granular carbon or pulverized carbon.

5. The process of claim 1, wherein the content of the phenothiazine in the (meth)acrylic monomer after adsorption is less than 5 ppm.

6. The process of claim 1, wherein the moderately active polymerization inhibitor is hydroquinone monomethyl ether.

7. The process of claim 1, wherein a content of moderately active polymerization inhibitor is up to 100 ppm.

8. The process of claim 1, wherein a content of moderately active polymerization inhibitor is around 50 ppm.

9. The process of claim 1, wherein the (meth)acrylic monomer is a (meth)acrylic acid.

10. The process of claim 9, wherein the (meth)acrylic monomer is an acrylic acid.

11. The process of claim 10, wherein a water content of the acrylic acid is from 40 to 75% by weight.

12. The process of claim 10, wherein the acrylic acid is anhydrous.

13. The process of claim 10, wherein from 20 to 95 mol % of acid groups of the acrylic acid are neutralized.

14. The process of claim 10, wherein acid groups of the acrylic acid are unneutralized.

15. The process of claim 10, wherein from 40 to 75 mol % of acid groups of the acrylic acid are neutralized.

16. The process of claim 10, further comprising:
polymerizing the acrylic acid after adsorption, to obtain a superabsorbent polymer.

17. The process of claim 1, wherein removing phenothiazine comprises a fixed bed process.

18. The process of claim 1, further comprising regenerating the activated carbon.

* * * * *